(12) United States Patent
Takahashi

(10) Patent No.: US 9,974,718 B2
(45) Date of Patent: May 22, 2018

(54) METHOD FOR PREPARING HAIR CARE COMPOSITIONS COMPRISING A STEP OF ADDING PERFUMES AND/OR SILICONES BEFORE ANTIDANDRUFF AGENTS

(71) Applicant: The Procter & Gamble Company, Cincinnati, OH (US)

(72) Inventor: Kenji Takahashi, Takasaki (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

(21) Appl. No.: 14/174,362

(22) Filed: Feb. 6, 2014

(65) Prior Publication Data

US 2015/0216769 A1    Aug. 6, 2015

(51) Int. Cl.
| | | |
|---|---|---|
| *A61K 8/18* | (2006.01) | |
| *A61K 8/02* | (2006.01) | |
| *A61Q 5/00* | (2006.01) | |
| *A61K 8/41* | (2006.01) | |
| *A61Q 13/00* | (2006.01) | |
| *A61K 8/894* | (2006.01) | |
| *A61K 8/898* | (2006.01) | |

(52) U.S. Cl.
CPC ............ *A61K 8/0241* (2013.01); *A61K 8/416* (2013.01); *A61K 8/894* (2013.01); *A61K 8/898* (2013.01); *A61Q 5/006* (2013.01); *A61Q 13/00* (2013.01)

(58) Field of Classification Search
CPC . A61K 8/06; A61K 8/416; A61K 8/58; A61K 8/36; A61K 8/4946; A61Q 5/12; A61Q 5/006; A61Q 5/02; A61Q 5/06; A61Q 5/00; A61Q 5/002; A61Q 5/008; A61Q 13/00; A61Q 19/02
USPC ........................................... 424/70.12, 70.28
See application file for complete search history.

(56) References Cited

U.S. PATENT DOCUMENTS

| | | | |
|---|---|---|---|
| 4,275,055 A | 6/1981 | Nachtigal et al. | |
| 6,979,439 B1 | 12/2005 | Sakai et al. | |
| 2004/0191331 A1 | 9/2004 | Schwartz et al. | |
| 2007/0128147 A1 | 6/2007 | Schwartz et al. | |
| 2010/0015078 A1* | 1/2010 | Li | A61K 8/342 424/70.12 |
| 2010/0143280 A1 | 6/2010 | Yokogi et al. | |
| 2010/0143281 A1 | 6/2010 | Okada et al. | |
| 2010/0143282 A1 | 6/2010 | Yokogi et al. | |
| 2010/0143425 A1 | 6/2010 | Okada et al. | |
| 2012/0258067 A1* | 10/2012 | Yang | A61K 8/342 424/70.28 |
| 2012/0316239 A1 | 12/2012 | Okada et al. | |

FOREIGN PATENT DOCUMENTS

| | | |
|---|---|---|
| JP | 2010013404 A | 1/2010 |
| KR | 2001-0045153 | 11/1999 |
| WO | WO01/35912 | 5/2001 |

OTHER PUBLICATIONS

International Search Report; PCT/US2014/014992; dated Jun. 2, 2014.
Extra Fullness Dandruff Condition; Database GNPD Mintel Jul. 2004.
U.S. Appl. No. 14/174,317, filed Feb. 6, 2014, Kenji NMN Takahashi.
U.S. Appl. No. 14/174,377, filed Feb. 6, 2014, Kenji NMN Takahashi.
U.S. Appl. No. 14/174,389, filed Feb. 6, 2014, Kenji NMN Takahashi.
U.S. Appl. No. 14/174,401, filed Feb. 6, 2014, Kristine Suzanne So Yu.
U.S. Appl. No. 14/174,415, filed Feb. 6, 2014, Kristine Suzanne So Yu.
U.S. Appl. No. 14/174,433, filed Feb. 6, 2014, Kristine Suzanne So Yu.
All Office Actions, U.S. Appl. No. 14/174,317.
All Office Actions, U.S. Appl. No. 14/174,377.

* cited by examiner

*Primary Examiner* — Nannette Holloman
(74) *Attorney, Agent, or Firm* — Linda M. Sivik

(57) ABSTRACT

The present invention relates to a method of preparing a hair care composition comprising a step of adding perfume, silicone, phenoxyethanol, benzyl alcohol, and/or parabens perfumes and/or silicones, before adding antidandruff agents. Preferably, perfumes and/or silicones are added before adding antidandruff agents. The method of the present invention provides reduced agglomeration of antidandruff agent selected from metal pyrithiones.

9 Claims, 2 Drawing Sheets

METHOD FOR PREPARING HAIR CARE COMPOSITIONS COMPRISING A STEP OF ADDING PERFUMES AND/OR SILICONES BEFORE ANTIDANDRUFF AGENTS

FIELD OF THE INVENTION

The present invention relates to a method of preparing a hair care composition comprising a step of adding perfume, silicone, phenoxyethanol, benzyl alcohol, and/or parabens perfumes and/or silicones, before adding antidandruff agents. Preferably, perfumes and/or silicones are added before adding antidandruff agents. The method of the present invention provides reduced agglomeration of antidandruff agent selected from metal pyrithiones.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits. Furthermore, a variety of approaches have been developed to provide other benefits in addition to such conditioning benefits.

For example, some conditioning compositions provide antidandruff benefit in addition to conditioning benefits.

For example, WO2001/35912 discloses in Examples 7 and 9, hair conditioning compositions comprising 0.96% Cetyl alcohol, 0.64% of Stearyl alcohol, 1.0% of Ditallow dimethyl ammonium chloride, and 2.0% of zinc pyrithione. WO2001/35912 discloses that the above compositions are suitably made as follows:

"When included in the composition, polymeric materials such as polypropylene glycol are dispersed in water at room temperature to make a polymer solution, and heated up to above 70° C. Amidoamine and acid, and when present, other cationic surfactants, ester oil of low melting point oil are added in the solution with agitation. Then high melting point fatty compound, and when present, other low melting point oils and benzyl alcohol are also added in the solution with agitation. The mixture thus obtained is cooled down to below 60° C., and if present, the remaining components such as zinc pyrithione, silicone compound, and menthol are added with agitation, and further cooled down to about 30° C.

However, it has been found that, in such compositions containing zinc pyrithione, the zinc pyrithione often forms agglomeration. Such agglomerations, especially those having a larger particle sizes such as those of 400 microns or more may provide undesirable product appearance, and/or sticking to manufacturing equipment.

Thus, there remains a need for a method for preparing antidandruff hair conditioning compositions, to provide reduced agglomeration, especially reduced larger particle size of agglomeration of antidandruff agents, more specifically reduced such as those of 400 microns or more.

None of the existing art provides all of the advantages and benefits of the present invention.

SUMMARY OF THE INVENTION

The present invention is directed to a method of preparing a hair care compositions, wherein the composition comprises:

(a) A cationic surfactant system;
(b) A high melting point fatty compound;
(c) Aqueous carrier;
(d) An antidandruff agent selected from metal pyrithiones; and
(e) A perfume, silicone, phenoxyethanol, benzyl alcohol, and/or parabens;
and wherein the method comprises the steps of:
(1) Mixing the cationic surfactant system, high melting point fatty compound and aqueous carrier to form an emulsion;
(2) Adding the component (e) to the emulsion; and
(3) Then, adding the antidandruff agent (d).

The method of the present invention provides reduced agglomeration of the antidandruff agents, especially reduced larger particle size of agglomeration of the antidandruff agents. It is believed that, by reducing the agglomeration, the method/composition can provide improved deposition of the antidandruff agent.

These and other features, aspects, and advantages of the present invention will become better understood from a reading of the following description, and appended claims.

DETAILED DESCRIPTION OF THE INVENTION

Figure 1:
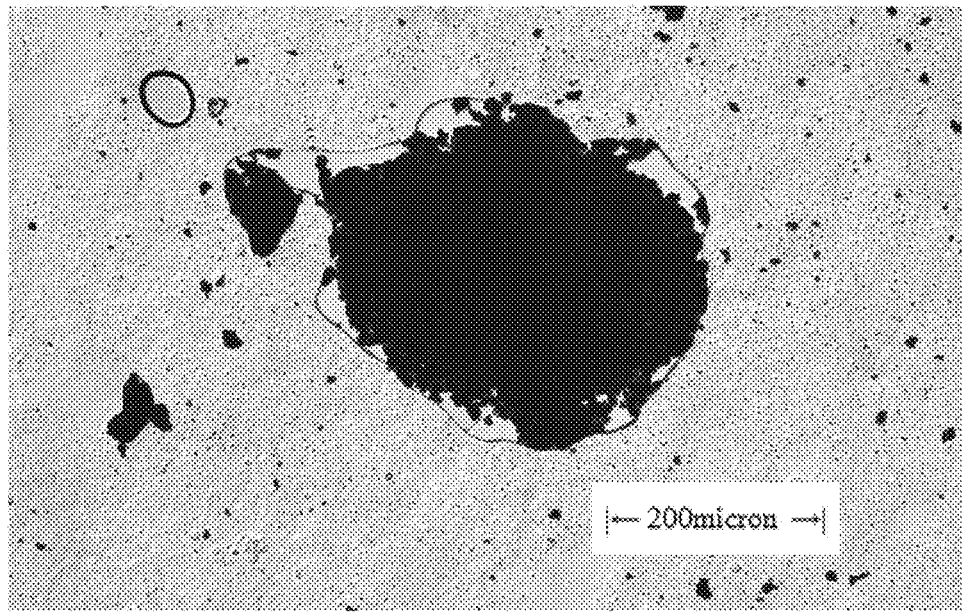
FIG. 1 is a photo of transmitted light image of the composition of Ex. 1

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The present invention is directed to a method of preparing a hair care compositions, wherein the composition comprises:

(a) A cationic surfactant system;
(b) A high melting point fatty compound;
(c) Aqueous carrier;
(d) An antidandruff agent selected from metal pyrithiones; and
(e) A perfume, silicone, phenoxyethanol, benzyl alcohol, and/or parabens;
and wherein the method comprises the steps of:
(1) Mixing the cationic surfactant system, high melting point fatty compound and aqueous carrier to form an emulsion;
(2) Adding the component (e) to the emulsion; and (3) Then, adding the antidandruff agent (d).

Component (e) is preferably a perfume and/or silicone. The emulsion is preferably gel matrix.

In the step (1), it is preferred to use a preferred method of forming an emulsion which is described later as E-METHOD-B in view of improved agglomeration reduction. Such preferred method of forming an emulsion comprising the steps of:

(1-B1) preparing an oil phase comprising the surfactant and the high melting point fatty compound, wherein the temperature of the oil phase is higher than a melting point of the high melting point fatty compound; and (1-B2) preparing an aqueous phase comprising the aqueous carrier, wherein the temperature of the aqueous phase is below the melting point of the high melting point fatty compounds; and (1-B3) mixing the oil phase and the aqueous phase to form an emulsion; wherein the step (1-B3) comprises the following further detailed steps:

(1-B3-1) feeding either of the oil phase or the aqueous phase into a high shear field having an energy density of about $1.0 \times 10^2$ J/m$^3$ or more;

(1-B3-2) feeding the other phase directly to the field; and (1-B3-3) forming an emulsion.

In the step (2), it is preferred to add the component (e) at levels of 20% or more of its total amount, more preferably 50% or more of its total amount, still more preferably 80% or more of its total amount, even more preferably 100% of its total amount.

In the step (3), it is preferred to add the antidandruff agent at levels of 20% or more of its total amount, more preferably 50% or more of its total amount, still more preferably 80% or more of its total amount, even more preferably 100% of its total amount.

It has been found that the above component (e) prior to the addition of antidandruff agents provides reduced agglomeration of the antidandruff agents.

Such addition order is preferably used in the following conditions, which is believed to form more agglomeration and/or larger agglomeration of the antidandruff agent:

When the cationic surfactant system contains a mono-long alkyl quaternized ammonium salt, especially the cationic surfactant system contains it at levels by weight of the composition from about 0.05%, especially from about 0.1%, more specifically from about 0.3%.

When the cationic surfactant system contains a di-long alkyl quaternized ammonium salt cationic surfactant, especially when the cationic surfactant system contains dicetyl dimethyl ammonium chloride, more specifically when the cationic surfactant system contains it at levels by weight of the composition from about 0.05%, especially from about 0.1%, more specifically from about 0.3%.

When the total level of the cationic surfactant system and high melting point fatty compound is 10.0% or less, more specially 8.0% or less, still more specifically 5.0% or less by weight of the composition;

When the composition further contains perfumes, especially when the perfume is that having a Dielectric Constant (DC) of 15 or lower, more specifically 12 or lower, still more specifically 10 or lower, at levels by weight of the composition of from about 0.01%, especially from about 0.05%, more specifically from about 0.1%, even more specifically from about 0.3%;

When the composition further contains a silicone compound, especially when the silicone compound has a hydrophilic group, more specifically when the silicone compounds are selected from the group consisting of aminosilicone, silicone copolyol, aminosilicone copolyol, quaternized silicone, quaternized silicone copolyol, and mixtures thereof, at levels by weight of the composition of from about 0.01%, especially from about 0.05%, more specifically from about 0.1%, even more specifically from about 0.3%; and Mixtures thereof.

Addition of Antidandruff Agents

Antidandruff agents are added to the emulsion having a temperature of preferably from about 40° C. to about 66° C., more preferably from about 45° C. to about 60° C., still more preferably from about 48° C. to about 55° C.

In the step (3), when the temperature of the emulsion is lower than the above temperature, the emulsion can be heated up to the above temperature, then the antidandruff agent is added to the emulsion. It is preferred, however, adding the antidandruff agent to the emulsion, without cooling the emulsion below the above temperature, in view of more effective reduction of agglomeration.

Hair Care Composition

The hair care composition of the present invention comprises a cationic surfactant system, high melting point fatty compound, and aqueous carrier, and an antidandruff agent. The surfactants, the high melting point fatty compounds, and the aqueous carrier are in the form of emulsion, preferably gel matrix. The hair care composition of the present invention further comprises a perfume, silicone, phenoxyethanol, benzyl alcohol, and/or parabens, preferably, perfume and/or silicone.

Cationic Surfactant System

The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt. More preferably, the cationic surfactant system is a mixture of mono-long alkyl quaternized ammonium salt and di-long alkyl quaternized ammonium salt.

Preferably, in the present invention, the surfactant is water-insoluble. In the present invention, "water-insoluble surfactants" means that the surfactants have a solubility in water at 25° C. of below 1 g/100 g water (excluding 1 g/100 water), preferably 0.7 g/100 g water or less, more preferably 0.5 g/100 g water or less, still more preferably 0.3 g/100 g water or less. The cationic surfactant system is included in the composition at a level by weight of from about 0.1% to about 10%, preferably from about 0.5% to about 8%, more preferably from about 0.8% to about 5%, still more preferably from about 1.0% to about 4%.

Mono-Long Alkyl Quaternized Ammonium Salt

The monoalkyl quaternized ammonium salt cationic surfactants useful herein are those having one long alkyl chain which has from 12 to 30 carbon atoms, preferably from 16 to 24 carbon atoms, more preferably C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

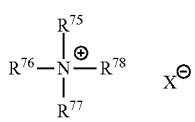

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

Di-alkyl cationic surfactants useful herein are those having two long alkyl chains of from 12 to 30 carbon atoms, more preferably from 16 to 24 carbon atoms, still more preferably from 16 to 22 carbon atoms, including, for example, di-long alkyl quaternized ammonium salts. Such di-alkyl quaternized ammonium salts useful herein are those having the formula (I):

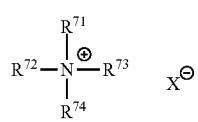

(I)

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 16 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Such preferred di-alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The high melting point fatty compound can be included in the composition at a level of from about 0.5%, preferably from about 1.0%, more preferably form about 1.5%, still more preferably from about 2%, even more preferably from about 4%, and to about 15%, preferably to about 10% by weight of the composition, in view of providing the benefits of the present invention.

The high melting point fatty compound useful herein have a melting point of 25° C. or higher, preferably 40° C. or higher, more preferably 45° C. or higher, still more preferably 50° C. or higher, in view of stability of the emulsion especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present invention, more preferred fatty alcohols are cetyl alcohol, stearyl alcohol and mixtures thereof.

Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan).

Gel Matrix

Preferably, in the present invention, the emulsion is in the form of a gel matrix. The gel matrix comprises the cationic surfactant system, the high melting point fatty compound, and an aqueous carrier. The gel matrix is suitable for providing various conditioning benefits, such as slippery feel during the application to wet hair and softness and moisturized feel on dry hair.

Preferably, especially when the gel matrix is formed, the total amount of the cationic surfactant and the high melting point fatty compound is from about 1.0%, preferably from about 2.0%, more preferably from about 3.0% by weight of the composition, in view of providing the benefits of the present invention, and to about 15%, preferably to about 14%, more preferably to about 13%, still more preferably to about 10% by weight of the composition, in view of spreadability and product appearance. Furthermore, when the gel matrix is formed, the cationic surfactant and the high melting point fatty compound are contained at a level such that the weight ratio of the cationic surfactant to the high melting point fatty compound is in the range of, preferably from about 1:1 to about 1:10, more preferably from about 1:1 to about 1:4, still more preferably from about 1:2 to about 1:4, in view of providing improved wet conditioning benefits.

Preferably, when the gel matrix is formed, the composition of the present invention is substantially free of anionic surfactants and anionic polymers, in view of stability of the gel matrix. In the present invention, "the composition being substantially free of anionic surfactants and anionic polymers" means that: the composition is free of anionic surfactants and anionic polymers; or, if the composition contains anionic surfactants and anionic polymers, the level of such anionic surfactants and anionic polymers is very low. In the present invention, a total level of such anionic surfactants and anionic polymers, if included, preferably 1% or less, more preferably 0.5% or less, still more preferably 0.1% or less by weight of the composition. Most preferably, the total level of such anionic surfactants and anionic polymers is 0% by weight of the composition.

Aqueous Carrier

The composition of the present invention comprises an aqueous carrier. The level and species of the carrier are selected according to the compatibility with other components, and other desired characteristic of the product.

The carrier useful in the present invention includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized water is preferably used. Water from natural sources including mineral cations can also be used, depending on the desired characteristic of the product. Generally, the compositions of the present invention comprise from about 20% to about 99%, preferably from about 30% to about 95%, and more preferably from about 80% to about 90% water.

Antidandruff Agent

The compositions of the present invention comprise an antidandruff agent selected from metal pyrithiones. The metal pyrithione can be included at a level by weight of the compositions of, preferably from about 0.01% to about 5%, more preferably from about 0.1% to about 3%, still more preferably from about 0.1% to about 2%.

Metal pyrithiones useful herein are heavy metal salts of 1-hydroxy-2-pyridinethione, the heavy metal salts being zinc, tin, cadmium, magnesium, aluminium, barium, bismuth, strontium, copper, and zirconium. Preferred heavy metals are zinc and copper. More preferred metal pyrithione is a zinc salt of 1-hydroxy-2-pyridinethione known in the art as zinc pyrithione, more preferably in a particle size of up to about 20 microns, still preferably from about 1 to about 10 microns.

Such metal pyrithione can be suspended by or coated by a polymer. Such polymer can be anionic polymers, nonionic polymers, and any other polymers. It may be preferred to use anionic polymers, more preferably sodium polynaphthalene sulfonate, still more preferably sodium polynaphthalene sulfonate having a tradename Darvanl Spray Dried, supplied from Vanderbilt Minerals having a molecular weight of about 3,000 g/mol in comparison to standards of sodium poly(styrenesulfonate) and a charge density of about 3.5-4 meq/g.

Metal Salt Other than Metal Pyrithione

The composition of the present invention may contain a metal salt other than metal pyrithiones. The metal salt is believed to improve antidandruff efficacy of metal pyrithione and/or help the composition to deliver clean benefit and/or hair volume benefit. The metal salt can be used at levels by weight of the composition of preferably from about 0.05% to about 10%, more preferably from about 0.1% to about 7%, still more preferably from about 0.5% to about 5% in view of delivering the above benefits.

This metal salt is preferably, a salt of a metal which is the same metal as that of the metal pyrithione. For example, when the metal pyrithione is zinc pyrithione, the metal salt is preferably zinc salt other than zinc pyrithione.

Such zinc salts include, for example, Zinc aluminate, Zinc carbonate, Zinc oxide, Zinc phosphates (i.e., orthophosphate and pyrophosphate), Zinc selenide, Zinc sulfide, Zinc silicates (i.e., ortho- and meta-zinc silicates), Zinc silicofluoride, Zinc Borate, Zinc hydroxide, zinc hydroxyl carbonate, hydrozincite (zinc carbonate hydroxide), basic zinc carbonate, aurichalcite (zinc copper carbonate hydroxide), rosasite (copper zinc carbonate hydroxide) and combinations thereof. Preferably, zinc salt are zinc hydroxyl carbonate, hydrozincite (zinc carbonate hydroxide), basic zinc carbonate, aurichalcite (zinc copper carbonate hydroxide), rosasite (copper zinc carbonate hydroxide) and combinations thereof. More preferably, zinc salt is hydrozincite (zinc carbonate hydroxide).

Preferably, such metal salt are those which remain mostly insoluble within formulated compositions. "Being insoluble within the formulated compositions" herein means that the material remains as solid particulates and do not dissolve in the formula.

D(90) is the particle size which corresponds to 90% of the amount of particles are below this size. The particulate of metal salt preferably have a particle size distribution wherein 90% of the particles are less than about 50 microns. In a further embodiment of the present invention, the particulate metal salt may have a particle size distribution wherein 90% of the particles are less than about 30 microns. In yet a further embodiment of the present invention, the particulate metal salt may have a particle size distribution wherein 90% of the particles are less than about 20 microns.

Perfume

The composition of the present invention preferably contains perfumes. Perfumes can be included at levels by the weight of the composition of preferably from about 0.01% to about 5.0%, from about 0.05% to about 3.0%, more preferably from about 0.1% to about 2.0%, still more preferably from about 0.2% to about 1.0%.

Silicone Compound

The compositions of the present invention preferably contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 1microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred. These silicone compounds are available, for example, from the General Electric Company in their Viscasil® and TSF 451 series, and from Dow Corning in their Dow Corning SH200 series.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

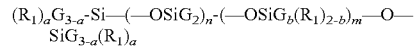

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $CqH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3$A$^-$; —N($R_2$)$CH_2$—$CH_2$—$NR_2H_2$A$^-$; wherein $R_2$ is hydrogen, phenyl, benzyl, or a saturated hydrocarbon radical, preferably an alkyl radical from about $C_1$ to about $C_{20}$; A$^-$ is a halide ion.

Highly preferred amino silicones are those corresponding to formula (I) wherein m=0, a=1, q=3, G=methyl, n is preferably from about 1500 to about 1700, more preferably about 1600; and L is —N($CH_3$)$_2$ or —$NH_2$, more preferably —$NH_2$. Another highly preferred amino silicones are those corresponding to formula (I) wherein m=0, a=1, q=3, G=methyl, n is preferably from about 400 to about 600, more preferably about 500; and L is —N($CH_3$)$_2$ or —$NH_2$, more preferably —$NH_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen, vitamin E, panthenol, panthenyl ethyl ether, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; sequestering agents, such as disodium ethylenediamine tetra-acetate; and ultraviolet and infrared screening and absorbing agents such as benzophenones.

Phenoxyethanol, Benzyl Alcohol, and/or Parabens Such as Methyl Paraben, Propyl Paraben.

When the composition contains these ingredients, they are added to the emulsion before adding the antidandruff agent.

Product Forms

The compositions of the present invention can be in the form of rinse-off products or leave-on products, and can be formulated in a wide variety of product forms, including but not limited to creams, gels, emulsions, mousses and sprays. The composition of the present invention is especially suitable for hair conditioners especially rinse-off hair conditioners.

The composition of the present invention can be used anytime, with or without shampooing. Especially when the composition is rinse-off conditioners, it is preferable used after shampooing the hair.

Method of Forming an Emulsion

The present invention comprises a step of mixing the cationic surfactant system, high melting point fatty compound and aqueous carrier to form an emulsion;

The emulsion can be prepared by any conventional method well known in the art. They can be prepared by the following preferred methods.

(A) Preferred Method of Forming an Emulsion (E-Method A)

A preferred method of forming an emulsion comprises the steps of:

(1-A1) mixing the cationic surfactant system, high melting point fatty compound and aqueous carrier wherein the temperature of the mixture is above the melting point of the high melting point fatty compounds; and (1-A2) The mixture is cooled down to form an emulsion.

In the step (1-A1), the temperature of the mixture is above the melting point of the high melting point fatty compounds, preferably above the melting point of the high melting point fatty compounds, cationic surfactant system, and mixtures thereof. Preferably the mixture has a temperature of from about 40° C., more preferably from about 50° C., still more preferably from about 60° C., even more preferably from about 70° C., further preferably from about 75° C., and to about 150° C., more preferably to about 100° C., still more preferably to about 90° C. In the step (1-A1), the cationic surfactant, high melting point fatty compounds can be added to the aqueous carrier at anytime at any temperature, as long as they are mixed at the above temperature. For example, the cationic surfactant, high melting point fatty compounds can be added to the aqueous carrier at a lower temperature than the above temperature, then heated up to the above temperature, and mixed at the above temperature. Alternatively, warmed and melted cationic surfactants and/or high melting point fatty compounds can be added to warmed water, and mixed without further heating up.

In the step (1-A2), the mixture is cooled down to form gel matrix.

In the step (1-A2), it is preferred that the mixture is gradually cooled down, at a rate of from about 1° C. to 10° C./minute, more preferably from about 1° C. to 5° C./minute.

(B) Preferred Method of Forming an Emulsion (E-Method B)

Another preferred method of forming an emulsion comprises the steps of:
(1-B1) preparing an oil phase comprising the surfactant and the high melting point fatty compound, wherein the temperature of the oil phase is higher than a melting point of the high melting point fatty compound; and
(1-B2) preparing an aqueous phase comprising the aqueous carrier, wherein the temperature of the aqueous phase is below the melting point of the high melting point fatty compounds; and
(1-B3) mixing the oil phase and the aqueous phase to form an emulsion; wherein the mixing step (1-B3) comprises the following detailed steps:
(1-B3-1) feeding either of the oil phase or the aqueous phase into a high shear field having an energy density of about $1.0 \times 10^2$ J/m$^3$ or more;
(1-B3-2) feeding the other phase directly to the field; and
(1-B3-3) forming an emulsion;
the mixing step (1-B3) is conducted by using a homogenizer having a rotating member.

E-Method B—Details of Mixing Step (1-B3)

In the E-METHOD B, by directly feeding the phase to the high shear field, the oil phase and the aqueous phase first meet in the high shear field. It is believed that, by meeting first in the high shear field, the E-METHOD B provides improved transformation of surfactants and high melting point fatty compounds to emulsions, i.e., the resulted compositions contain reduced amount of non-emulsified surfactants/high melting point fatty compounds, compared to other methods by which such phases first meet in non- or lower shear field. It is also believed that, by such improved transformation to an emulsion, the E-METHOD B provides the resulted composition with improved conditioning benefits, and may also provide them with improved product appearance and/or product stability.

"Direct feeding" herein means, feeding the two phases such that the two phases can reach to the high shear field after first meeting, within 0.52 seconds or less, preferably 0.5 seconds or less, more preferably 0.3 seconds or less, still more preferably 0.1 seconds or less, even more preferably 0 second, in view of improved transformation to emulsions. In the present invention, the direct feeding is preferably conducted by a direct injection.

"High shear field" herein means that the field has an energy density of from about $1.0 \times 10^2$ J/m$^3$, preferably from about $1.0 \times 10^3$ J/m$^3$, more preferably from about $1.0 \times 10^4$ J/m$^3$ in view of improved transformation to emulsions, and to about $5.0 \times 10^8$ J/m$^3$, preferably to about $2.0 \times 10^7$ J/M$^3$, more preferably to about $1.0 \times 10^7$ J/m$^3$.

In E-METHOD B, it is preferred that the mixing step (1-B3) comprises the following detailed steps:
(1-B3-1) feeding the aqueous phase into a high shear field having an energy density of $1.0 \times 10^2$ J/m$^3$ or more;
(1-B3-2) feeding the oil phase directly to the field; and
(1-B3-3) forming an emulsion.

In E-METHOD B, especially when using homogenizers having a rotating member described below in detail, it is preferred to feed the oil phase into the high shear field in which the aqueous phase is already present, in view of stably manufacturing the compositions with improved conditioning benefits.

Preferably, the mixing step (1-B3) including the detailed steps (1-B3-1) and (1-B3-2) is conducted by using a high shear homogenizer.

It is known that high shear homogenizers include, for example: high shear homogenizers having a rotating member; and high pressure homogenizers. In the present invention, high shear homogenizers having a rotating member are used, rather than high pressure homogenizers such as Sonolator® available from Sonic Corporation, Manton Gaulin type homogenizer available from the APV Manton Corporation, and Microfluidizer available from Microfluidics Corporation. Such a high shear homogenizer having a rotating member is believed to: provide more flexibility of manufacturing operation by its two independent operation levers (flow rate and rotating speed) while high pressure homogenizers have only one lever (pressure determined depending on flow rate); and/or require less investment for high pressure.

High shear homogenizers having a rotating member useful herein include, for example, direct injection rotor-stator homogenizers such as: Becomix® available from A. Berents Gmbh&Co. and Lexa-30 available from Indolaval/TetraPac, in view of improved transforming to emulsions. These direct injection rotor-stator homogenizers are preferred since the two phases can quickly reach to the high shear field after first meeting, compared to other homogenizers having a rotating member, when used as-is. Such other homogenizers having a rotating member include, for example: T. K. pipeline homomixer available from Primix Corporation, and DR-3 available from IKA Corporation. Those other homogenizers having a rotating member might be used with modifications such that the two phases can quickly reach to the high shear field after first meeting. Such other homogenizers having a rotating member, when used as-is, may provide an increased amount of high melting point fatty compound crystals which are not transformed into emulsions, in the composition. Other homogenizers, which has a lower energy density, such as that named T. K. pipeline homomixer may also provide such an increased amount of high melting point fatty compound crystals.

E-Method B—Details of Temperature Conditions

In the E-METHOD B, the oil phase has a temperature which is higher than a melting point of the high melting point fatty compounds. Preferably, the oil phase has a temperature which is higher than a melting point of the oil phase. Preferably, the oil phase has a temperature of from about 25° C., more preferably from about 40° C., still more preferably from about 50° C., even more preferably from about 55° C., further preferably from about 66° C., and to about 150° C., more preferably to about 95° C., still more preferably to about 90° C., even more preferably to about 85° C., when mixing it with the aqueous phase.

In the present invention, the aqueous phase has a temperature which is below the melting point of the high melting point fatty compounds. Preferably, the aqueous phase has a temperature of from about 10° C., more preferably from about 15° C., still more preferably from about 20° C., and to about 65° C., more preferably to about 55° C., still more preferably to about 52° C., when mixing it with the oil phase. Preferably, the temperature of the aqueous phase, when mixing it with the oil phase, is at least about 5° C. lower than, more preferably at least about 10° C. lower than the temperature of the oil phase. Preferably, the temperature of the aqueous phase, when mixing it with the oil phase, is from about 2° C. to about 60° C. lower than, more preferably from about 2° C. to about 40° C. lower than, still more preferably from about 2° C. to about 30° C. lower than the melting point of the high melting point fatty compounds.

Preferably, especially when forming a gel matrix, the temperature of the emulsion when formed is from about 2° C. to about 60° C. lower than, more preferably from about 2° C. to about 40° C. lower than, still more preferably from about 2° C. to about 30° C. lower than the melting point of the high melting point fatty compounds.

E-Method B—Details of Oil Phase Composition

Oil phase comprises the surfactants and the high melting point fatty compounds. The oil phase comprises preferably from about 50% to about 100%, more preferably from about 60% to about 100%, still more preferably from about 70% to about 100% of the surfactants and the high melting point fatty compounds, by weight of the total amount of the surfactants and the high melting point fatty compounds used in the personal care composition, in view of providing the benefits of the E-METHOD B.

The surfactants and the high melting point fatty compounds are present in the oil phase, with or without other ingredients, at a level by weight of the oil phase of, preferably from about 35% to about 100%, more preferably from about 50% to about 100%, still more preferably from about 60% to about 100%, in view of providing the benefits of the E-METHOD B.

Oil phase may contain an aqueous carrier such as water and lower alkyl alcohols, and polyhydric alcohols. If included, the level of aqueous carrier in the oil phase is up to about 50%, more preferably up to about 40%, still more preferably up to about 25%, even more preferably up to about 15% by weight of the oil phase, in view of providing the benefits of the E-METHOD B. Among the aqueous carrier, it is further preferred to control the level of water in oil phase, such that the level of water in oil phase is preferably up to about 40%, more preferably up to about 25%, still more preferably up to about 15%, even more preferably up to about 10% by weight of the oil phase. The oil phase may be substantially free of water. In the present invention, "oil phase being substantially free of water" means that: the oil phase is free of water; the oil phase contains no water other than impurities of the ingredients; or, if the oil phase contains water, the level of such water is very low. In the present invention, a total level of such water in the oil phase, if included, preferably 1% or less, more preferably 0.5% or less, still more preferably 0.1% or less by weight of the oil phase.

Oil phase may contain other ingredients than the surfactants and the high melting point fatty compounds and aqueous carrier. Such other ingredients are, for example, water-insoluble components and/or heat sensitive components, such as water-insoluble preservatives such as parabens and non-heat sensitive preservatives such as benzyl alcohol. In the E-METHOD B, "water-insoluble components" means that the components have a solubility in water at 25° C. of below 1 g/100 g water (excluding 1 g/100 water), preferably 0.7 g/100 g water or less, more preferably 0.5 g/100 g water or less, still more preferably 0.3 g/100 g water or less. If included, it is preferred that the level of such other ingredients in the oil phase is up to about 50%, more preferably up to about 40%, by weight of the oil phase, in view of providing the benefits of the E-METHOD B.

E-Method B—Details of Aqueous Phase Composition

Aqueous phase comprises aqueous carrier. The aqueous phase comprises preferably from about 50% to about 100%, more preferably from about 70% to about 100%, still more preferably from about 90% to about 100%, even more preferably from about 95% to about 100% of aqueous carrier, by weight of the total amount of the aqueous carrier used in the hair care composition, in view of providing the benefits of the E-METHOD B.

Aqueous carrier is present in the aqueous phase, with or without other ingredients, at a level by weight of the aqueous phase of, from about 50% to about 100%, more preferably from about 70% to about 100%, still more preferably from about 90% to about 100%, even more preferably from about 95% to about 100%, in view of providing the benefits of the E-METHOD B.

Aqueous phase may contain the surfactants and high melting point fatty compounds. If included, it is preferred that the level of the sum of the surfactants and high melting point fatty compounds in the aqueous phase is up to about 20%, more preferably up to about 10%, still more preferably up to about 7% by weight of the aqueous phase, in view of providing the benefits of the E-METHOD B. Even more preferably, the aqueous phase is substantially free of the surfactants and high melting point fatty compounds. In the E-METHOD B, "aqueous phase being substantially free of the surfactants and high melting point fatty compounds" means that: the aqueous phase is free of the surfactants and high melting point fatty compounds; or, if the aqueous phase contains the surfactants and high melting point fatty compounds, the level of such surfactants and high melting point fatty compounds is very low. In the E-METHOD B, a total level of such surfactants and high melting point fatty compounds in the aqueous phase, if included, preferably 1% or less, more preferably 0.5% or less, still more preferably 0.1% or less by weight of the aqueous phase.

Aqueous phase may contain other ingredients than the surfactants and the high melting point fatty compounds and aqueous carrier. Such other ingredients are, for example, water soluble components and/or heat sensitive components, such as water soluble pH adjusters, water soluble preservatives such as phenoxyethanol and Kathon®, and water soluble polymers. In the E-METHOD B, "water soluble components" means that the components have a solubility in water at 25° C. of at least 1 g/100 g water, preferably at least 1.2 g/100 g water, more preferably at least 1.5 g/100 g water, still more preferably at least 2.0 g/100 water. If included, it is preferred that the level of such other ingredients in the aqueous phase is up to about 20%, more preferably up to about 10% by weight of the aqueous phase, in view of providing the benefits of the E-METHOD B.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Compositions (Wt %)

Figure 2:
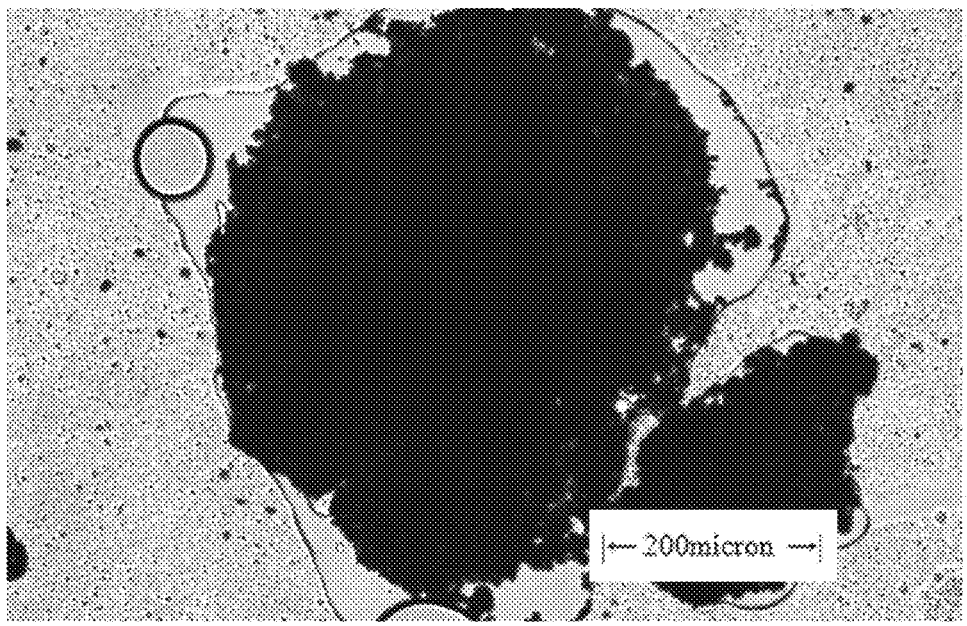
FIG. 2 is a photo of transmitted light image of the composition of CEx. i
Figure 3:
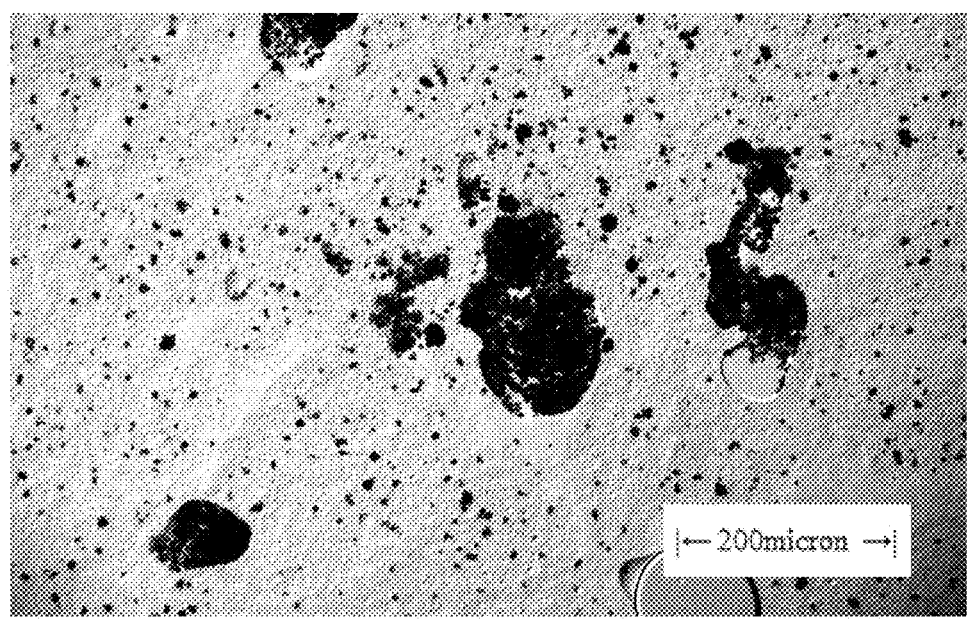
FIG. 3 is a photo of transmitted light image of the composition of Ex. 2
Figure 4:
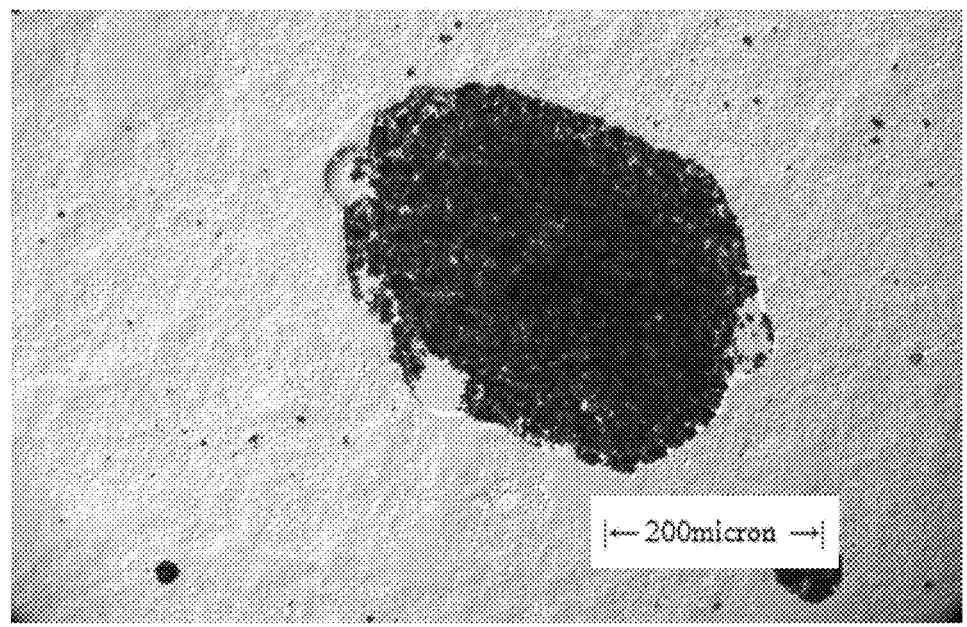
FIG. 4 is a photo of transmitted light image of the composition of CEx. ii

| | Components | Ex.1 | Ex.2 | Ex.3 | Ex. 4 | CEx. i | CEx. ii |
|---|---|---|---|---|---|---|---|
| Group O | Behenyl trimethylammonium methosulfate | 1.2 | 1.2 | — | 2.5 | 1.2 | 1.2 |
| | Stearamidopropyl dimethyl amine | — | — | 1.2 | — | — | — |
| | Dicetyl dimethyl ammonium chloride | 0.35 | 0.35 | 0.4 | — | 0.35 | 0.35 |
| | Cetyl alcohol | 1.0 | 1.0 | 2.0 | 1.0 | 1.0 | 1.0 |
| | Stearyl alcohol | 2.3 | 2.3 | 3.6 | 2.4 | 2.3 | 2.3 |
| | Benzyl alcohol | 0.4 | 0.4 | 0.4 | 0.4 | 0.4 | 0.4 |
| Group W | Deionized Water | q.s. to 100% of the composition | | | | | |
| | L-glutamic acid | — | — | 0.384 | — | — | — |
| | Preservative (Kathon CG) | 0.0666 | 0.0666 | 0.0666 | 0.0666 | 0.0666 | 0.0666 |
| Group Z | Zinc pyrithione *1 | 0.75 | 0.75 | 0.5 | 0.75 | 0.75 | 0.75 |
| Group P/S | Aminosilicone *2 | 0.75 | 0.75 | — | 0.5 | 0.75 | 0.75 |
| | Dimethicone *3 | — | — | 0.75 | — | — | — |
| | Perfume-1 *4 | 0.5 | 0.5 | — | 0.5 | 0.5 | 0.5 |
| | Perfume-2 *5 | — | — | 0.5 | — | — | — |
| Others | Panthenol | — | — | 0.05 | — | — | — |
| | Panthenyl ethyl ether | — | — | 0.03 | — | — | — |
| | Method of preparation | I | II | II | II | I-C | II-C |
| | Agglomeration | FIG. 1 | FIG. 3 | — | — | FIG. 2 | FIG. 4 |

Definitions of Components
*1 Zinc pyrithione: having a particle size of from about 1 to about 10 microns
*2 Aminosilicone: Available from GE having a viscosity 10,000 mPa·s, and having following formula (I):

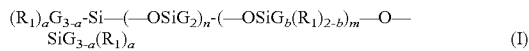

$$(R_1)_a G_{3-a}\text{-Si}-(-OSiG_2)_n-(-OSiG_b(R_1)_{2-b})_m-O-SiG_{3-a}(R_1)_a \quad (I)$$

wherein G is methyl; a is an integer of 1; b is 0, 1 or 2, preferably 1; n is a number from 400 to about 600; m is an integer of 0; $R_1$ is a monovalent radical conforming to the general formula $CqH_{2q}L$, wherein q is an integer of 3 and L is $-NH_2$

*3 Dimethicone: having a viscosity of 10,000 cSt
*4 Perfume-1: that having a DC of about 8.5
*5 Perfume-2: that having a DC of about 7.4

Method of Preparation

The above hair care compositions of "Ex. 1" through "Ex. 4" and "CEx. i" through "CEx.ii" were prepared by one of the following Methods I, I-C, II or II-C as shown above.

Method I, Including E-Method A

Groups O and W components are mixed with agitation, and heated to about 80° C. The mixture is cooled down to about 30° C. and gel matrix is formed. Group P/S components are added to the gel matrix with agitation. If included, other components are added to the gel matrix with agitation. Then, Group Z components are added with agitation at a temperature of about 30° C. Then the composition is cooled down to room temperature.

Method I-C, Including E-Method A.

Groups O and W components are mixed with agitation, and heated to about 80° C. The mixture is cooled down to about 30° C. and gel matrix is formed. Groups Z components are added to the gel matrix with agitation at a temperature of about 30° C. Then, Group P/S components are added with agitation. If included, other components are added to the gel matrix with agitation. Then the composition is cooled down to room temperature.

Method II, Including E-Method B

Group O components are mixed and heated to from about 66° C. to about 85° C. to form an oil phase. Separately, Group W components are mixed and heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ J/m$^3$ to $1.0 \times 10^7$ J/m$^3$ where the aqueous phase is already present. Group P/S components are added to the gel matrix with agitation. If included, other components are added to the gel matrix with agitation. Then, Group Z components are added with agitation at a temperature of about 50° C. Then the composition is cooled down to room temperature.

Method II-C, Including E-Method B

Group O components are mixed and heated to from about 66° C. to about 85° C. to form an oil phase. Separately, Group W components are mixed and heated to from about 20° C. to about 48° C. to form an aqueous phase. In Becomix® direct injection rotor-stator homogenizer, the oil phase is injected and it takes 0.2 second or less for the oils phase to reach to a high shear field having an energy density of from $1.0 \times 10^5$ J/m$^3$ to $1.0 \times 10^7$ J/m$^3$ where the aqueous phase is already present. Groups Z components are added to the gel matrix with agitation at a temperature of about 50° C. Then, Group P/S components are added with agitation. If included, other components are added to the gel matrix with agitation. Then the composition is cooled down to room temperature.

Properties and Benefits

For some of the above compositions, agglomeration is evaluated by the following methods. Results of the evaluation are also shown above in Table and FIG. 1-4.

Examples 1 through 4 are hair care compositions made by the methods of the present invention which are particularly useful for rinse-off use. The embodiments disclosed and represented by the previous "Ex. 1" through "Ex.4" have many advantages. For example, they provide reduced agglomeration of antidandruff agents.

Such advantages can be understood by the comparison between the examples of the present invention and comparative examples "CEx. i" and "CEx. ii"

For example, comparison between Ex. 1 (FIG. 1) and CEx. i (FIG. 2) shows that Ex. 1 (FIG. 1) shows reduced agglomeration of zinc pyrithione, compared to CEx. i (FIG. 2) which uses almost identical composition and method to Ex. 1 except for adding zinc pyrithione before adding perfumes and silicones. Also, comparison between Ex. 2 (FIG. 3) and CEx. ii (FIG. 4) shows that Ex. 2 (FIG. 3) shows reduced agglomeration of zinc pyrithione, compared to CEx. ii (FIG. 4) which uses almost identical composition and method to Ex. 2 except for adding zinc pyrithione before adding perfumes and silicones.

Agglomeration

Agglomeration is evaluated by direct visual evaluation of 100 magnifications of transmitted light image of the composition in which agglomeration is shown in black color. Photographs of such transmitted light image are shown in FIG. 1-4.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a hair care compositions, wherein the composition comprises:
    (a) a cationic surfactant system wherein the cationic surfactant system comprises a mono-long alkyl quaternized ammonium salt comprising one long alkyl chain which has from 12 to 30 carbon atoms and a di-long alkyl quaternized ammonium salt comprising two long alkyl chains of from 12 to 30 carbon atoms;
    (b) a high melting point fatty compound wherein the high melting point fatty compound has a melting point of 25° C. or higher;
    (c) an aqueous carrier;
    (d) an antidandruff agent selected from metal pyrithiones; and
    (e) a perfume, silicone, phenoxyethanol, benzyl alcohol, and/or parabens;
    and wherein the method comprises the steps of:
    (1) mixing the cationic surfactant system, high melting point fatty compound and aqueous carrier to form an emulsion;
    (2) adding the component (e) to the emulsion; and
    (3) then, adding the antidandruff agent (d).

2. The method of claim 1, wherein the component (e) is a perfume and/or silicone.

3. The method of claim 1, wherein the perfume has a Dielectric Constant (DC) of 15 or lower.

4. The method of claim 1, wherein the silicone compound has a hydrophilic group.

5. The method of claim 4, wherein the silicone compound is selected from the group consisting of aminosilicone, silicone copolyol, aminosilicone copolyol, quaternized silicone, quaternized silicone copolyol, and mixtures thereof.

6. The method of claim 1, wherein the total level of the cationic surfactant system and high melting point fatty compound is 10.0% or less.

7. The method of claim 1, wherein the step (1) comprises the following detailed steps:
    (1-B1) preparing an oil phase comprising the surfactant and the high melting point fatty compound, wherein the temperature of the oil phase is higher than a melting point of the high melting point fatty compound; and
    (1-B2) preparing an aqueous phase comprising the aqueous carrier, wherein the temperature of the aqueous phase is below the melting point of the high melting point fatty compounds; and
    (1-B3) mixing the oil phase and the aqueous phase to form an emulsion;
    wherein the step (1-B3) comprises the following further detailed steps:
    (1-B3-1) feeding either of the oil phase or the aqueous phase into a high shear field having an energy density of from about $1.0 \times 10^2$ J/m$^3$ to about $5.0 \times 10^8$ J/m$^3$;
    (1-B3-2) feeding the other phase directly to the field; and
    (1-B3-3) forming an emulsion.

8. The method of claim 7, wherein the step (1-B3) is conducted by using a homogenizer having a rotating member.

9. A composition made by the method of claim 1.

* * * * *